United States Patent
Badali et al.

(10) Patent No.: US 10,282,499 B2
(45) Date of Patent: May 7, 2019

(54) METHOD AND APPARATUS FOR X-RAY IONIZING RADIATION CONTROL

(71) Applicant: Triple Ring Technologies, Inc., Newark, CA (US)

(72) Inventors: Daniel Salvatore Badali, Fremont, CA (US); Tobias Funk, Martinez, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 318 days.

(21) Appl. No.: 15/382,536

(22) Filed: Dec. 16, 2016

(65) Prior Publication Data

US 2017/0177763 A1    Jun. 22, 2017

Related U.S. Application Data

(60) Provisional application No. 62/269,679, filed on Dec. 18, 2015.

(51) Int. Cl.
| | |
|---|---|
| H05G 1/30 | (2006.01) |
| G06F 17/50 | (2006.01) |
| G05B 13/04 | (2006.01) |
| A61L 2/08 | (2006.01) |

(52) U.S. Cl.
CPC .......... *G06F 17/5009* (2013.01); *A61L 2/082* (2013.01); *G05B 13/04* (2013.01); *H05G 1/30* (2013.01); *A61L 2202/14* (2013.01)

(58) Field of Classification Search
CPC .............................. G06F 17/5009; H05G 1/30
See application file for complete search history.

(56) References Cited

U.S. PATENT DOCUMENTS

2014/0315742 A1* 10/2014 Blakely ............ G01N 33/56972
  506/9
2018/0113083 A1*  4/2018 Van Dael ................ G01N 23/18

* cited by examiner

*Primary Examiner* — Douglas M Menz
(74) *Attorney, Agent, or Firm* — Joseph T. Lin (57) ABSTRACT

The present invention pertains to a method and apparatus for x-ray ionizing radiation control and ionizing radiation control. A digital representation of an inanimate object is formed. The amount of the radiation at a surface of the inanimate object is simulated. The radiation-matter interaction for a material of the inanimate object is calculated. The amount of energy deposited at a plurality of locations at the inanimate object is calculated. The digital representation of the inanimate object is modified in response to an input from a user and the modified digital representation of the inanimate object is displayed.

20 Claims, 6 Drawing Sheets

METHOD AND APPARATUS FOR X-RAY IONIZING RADIATION CONTROL

RELATED U.S. APPLICATION

This application claims priority to the co-pending U.S. provisional patent application, Ser. No. 62/269,679, entitled "METHOD FOR RADIATION STERILIZATION OF PRODUCT AND PACKAGING," with filing date Dec. 18, 2015 which is incorporated by reference herein in its entirety.

FIELD OF THE INVENTION

The present invention relates to ionizing radiation control systems. More particularly, the present invention pertains to a method and apparatus for x-ray ionizing radiation control.

BACKGROUND

Sterilization is a regulatory requirement for medical devices and health-care products. As sterilization is often also performed on foodstuffs, spacecraft materials, mail, pharmaceuticals, and other products, the term "product" will herein be used to refer to any object which is sterilized.

Although many sterilization methods are currently available, exposure to an intense beam of ionizing radiation is becoming increasing popular. This is particularly true in the medical device and pharmaceutical industries. The term "ionizing radiation" refers to any type of radiation that has enough energy to remove electrons from the atoms in a material. Some of the most common types of ionizing radiation are high energy electrons, gamma rays and x-rays.

The physical mechanism behind sterilization with such radiation is inelastic scattering: when the incident particle (e.g. a photon, electron, etc.) interacts with the material in the product, it transfers energy to the product at the location of the interaction. This is quantified in terms of dose, which is calculated as the amount of deposited energy divided by the local mass. Ionizing radiation can also be used for crosslinking of polymers and treatment and neutralization of hazardous waste.

The sterilization of medical devices and health care products by radiation is governed by the International Organization for Standardization (ISO), and is regulated by the ISO 11137 standard. This document specifies that the dose received by the product must be sufficiently high to achieve a sterility assurance level (SAL) of 10-6 (that is, the probability of a non-sterile unit is 1 in 1,000,000). At the same time, the dose must not be so high as to negatively affect the product's functionality. This imposes a narrow range of dose which the product can receive. Similarly, for polymer crosslinking applications, the dose received by the product must be sufficiently high to achieve adequate level of crosslinking but not be so high as to overly harden or embrittle the polymer.

In a typical product design process, testing to ensure that the sterilization regulations are met is only performed after the product has been fully designed, built, tested, and readied for mass production. There is an inherent risk to this approach, namely that a large amount of effort and resources have been invested in a product that may or may not make it to production, depending on the outcome of the sterilization tests.

What is needed is a cost-effective ionizing radiation control system capable of streamlining product design and minimizing redesign due to outcome of testing for sterilization, crosslinking or hazardous waste. Furthermore, the ionizing radiation control system should have speed and performance characteristics allowing for fast processing times.

SUMMARY

The present invention pertains to a method and apparatus for ionizing radiation control. A digital representation of an inanimate object is formed. The amount of the radiation at a surface of the inanimate object is simulated. The radiation-matter interaction for a material of the inanimate object is calculated. The amount of energy deposited at a plurality of locations at the inanimate object is calculated. The digital representation of the inanimate object is modified in response to an input from a user and the modified digital representation of the inanimate object is displayed. The plurality of locations can be located at the surface of the inanimate object. The amount of energy deposited at each of the plurality of locations can be compared against a dose threshold required to achieve sterilization of the material.

Under another embodiment of the present invention, a second digital representation of a packaging device of a second material around the inanimate object can be formed and the effect of the packaging device on the amount of energy deposited at each of the plurality of locations can be simulated. The position of the modified digital representation of the inanimate object can be changed and the amount of energy deposited at each of the plurality of locations at the inanimate object in the changed position can be calculated. The amount of energy deposited at each of the plurality of locations at the inanimate object can be compared against a dose threshold required to achieve adequate crosslinking of the material. The amount of energy deposited at each of the plurality of locations can be compared against a dose threshold required to achieve neutralization of hazardous waste on the material.

Under another embodiment of the present invention, a second digital representation of a radiation shield of a second material can be formed and the effect of the radiation shield on the amount of energy deposited at each of the plurality of locations can be simulated. The dose or the fluence of the radiation can be varied. The probability distribution of the x-ray radiation on the surface of the inanimate object can be calculated. A three dimensional digital representation of the inanimate object can be formed. A three dimensional digital model representing the inanimate object from a plurality of solid surfaces can be formed. The amount of x-ray radiation at a second plurality of locations on an interior surface of the inanimate object can be simulated and the amount of energy deposited at the second plurality of locations on the interior surface can be calculated.

Under another embodiment of the present invention, a system for ionizing radiation control comprises a display device for displaying a digital representation of an inanimate object to a user, a simulator to simulate amount of radiation at a surface of the inanimate object, a processor to calculate radiation matter-interaction for a material of the inanimate object and to calculate amount of energy deposited at the plurality of locations, a user input device for receiving input from said user, and a design tool to modify the digital representation of the inanimate object in response to input from the user. The system can comprise a second digital representation of packaging around the inanimate object. The system can comprise a three dimensional digital model representing the inanimate object formed from a plurality of solid surfaces. The system can comprise an interior surface in the three dimensional digital model. The system can comprise an indicator configured to indicate sufficient sterilization of the inanimate object.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
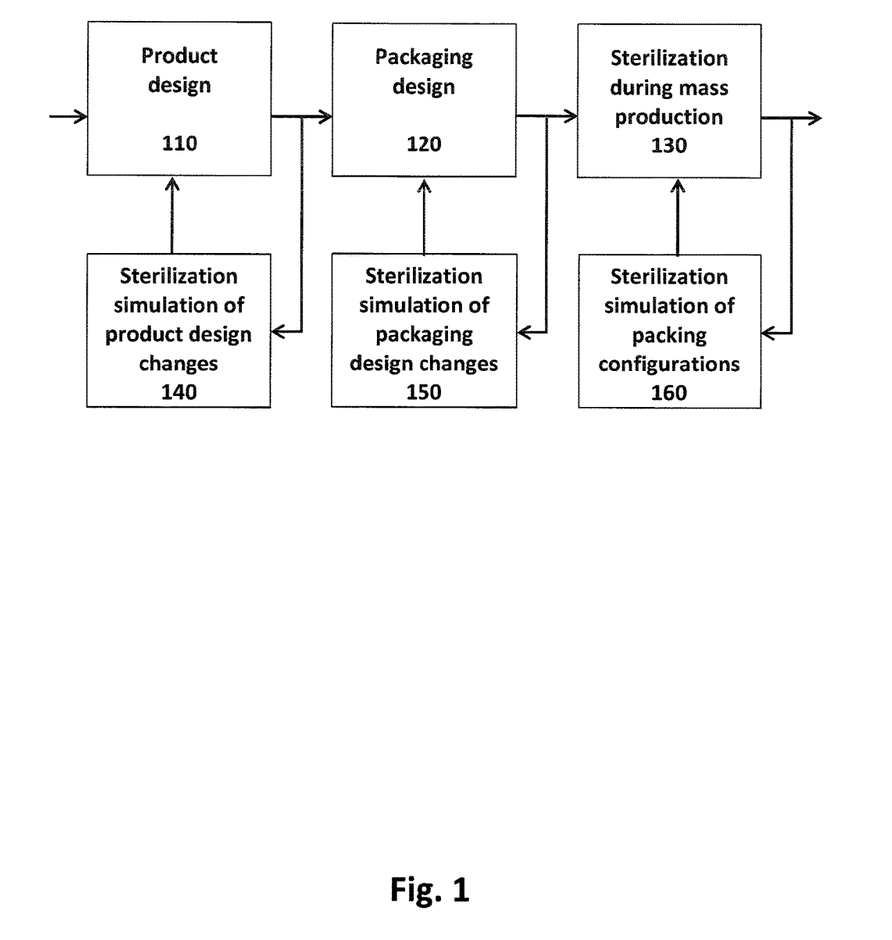
FIG. 1 is a flow diagram showing sterilization simulation of one embodiment of the present invention.

FIG. 1 is a flow diagram showing sterilization simulation of one embodiment of the present invention. A system is provided for hedging against this risk by incorporating computer simulations directly into the product development process to predict the outcome of the sterilization tests. In particular, a validated computer program is used and designed to virtually imitate the realistic radiation sterilization conditions. Performing such simulations regularly during product development provides rapid feedback on the influence of any design changes on the dose distribution throughout the device. In this way, the product's ability to pass the sterilization regulations can be anticipated and managed.

Such sterilization simulations can guide several phases of the product development, as listed below:
1. The design and engineering of the product 110
2. The design and engineering of the packaging 120 and placement of the product within the packaging
3. The choice of the appropriate sterilization method
4. The choice of the packing configuration for the final sterilization during mass production 130

These particular instances are presented by way of example and not by way of limitation. Some of these phases are illustrated in a flowchart in FIG. 1, which shows the role of the sterilization simulations in the product development process.

The computer simulations included virtually imitate the sterilization process by simulating the interaction between the incident radiation and the matter in the product. One way to do this is with the Monte Carlo technique, which sequentially tracks the trajectories of a large number of incident particles (electrons, photons, etc.) and statistically determines how they interact with the material. By recording how much energy is deposited in each location, such simulations have access to the full, three-dimensional distribution of dose within the product, as well as the accumulated dose received by individual components within the product. This information could be stored, for instance, in a three-dimensional voxel array, where each voxel contains the dose received by the product at that location.

Certain embodiments of the invention use a Monte Carlo simulator, although in general any type of simulation method can be used. Additionally, the dose values do not necessarily need to be calculated on a voxel-by-voxel basis. In general, the computer simulations are required to have a method to calculate the dose distribution within a product or the accumulated dose received by a specific component of the product. For example, if the Geant4 Monte Carlo simulation engine is used, the dose received by an individual component could be calculated using Geant4's "Sensitive Detector" construction. In this way, if a dosimeter is included in the virtual model of the product, the dose received by the dosimeter can be simulated.

To ensure that the simulations closely match the true radiation sterilization conditions, information such as the radiation beam parameters, experimental geometry, product geometry, and product materials are input into the simulator. Additionally, the simulator must have a way to realistically represent the product. A method is included to represent the product in a virtual form, either by using constructive solid geometry (e.g. Boolean combinations of simple shapes) or by boundary representation (e.g. tessellated surfaces). In the latter case, a system is included to build a virtual representation of the product directly from computer-aided design (CAD) files (such as STEP, STL, etc.).

A computer system is included capable of supporting the simulations. This consists of a computer which stores and runs a computer program that performs the simulations. Such a computer system has access to enough memory to run the simulation and store its inputs and output. Certain embodiments of the invention will use a computer program which performs the simulations on a graphical processing unit (GPU), and in such cases the computer system will need access to such a GPU.

Each embodiment of this invention consists of the comparison of the simulated dose distribution with experimentally measured dose values. This could be performed on the product of interest, or on a phantom designed specifically for such a comparison. This comparison can serve two purposes: first, agreement between the simulated and measured dose values suffices to validate the simulator. Second, because some of the experimental parameters might be unknown or estimated (such as the beam characteristics), such a comparison can be used to tune the input parameters to the simulator until an acceptable agreement between the experiments and the simulations is achieved. An important characteristic of these simulations is that they do not necessarily reproduce absolute dose numbers. However, the relative changes of dose within the radiation field are correctly reproduced.

Dose measurements are performed using the established technique of strategically placing multiple dosimeters within the product and its packaging. The product is then sterilized following the radiation sterilization procedure, and the dose values are subsequently obtained from the dosimeters. The dosimeters can be any device that has a quantitative response to exposure to radiation.

Certain embodiments of this invention will perform these comparisons using a specially-designed phantom. Such a phantom could be a shaped piece of a well-known material with dosimeters placed in such a way to measure a particular, singular characteristic of the radiation beam. For instance, the phantom could have dosimeters placed along the width of the conveyor belt to provide a measurement of the transverse spatial distribution of radiation. By using such phantoms to compare simulated and experimental dose values, a method is included to measure parameters of the sterilization system and incorporate them into the simulation inputs.

In another embodiment of this invention, simulations are used to calculate the dose in regions of the product that are inaccessible to dose measurements. For example, sterility inside a needle (a region in which the dose cannot be measured) can be inferred by using a simulated dose distribution that was validated against dosimeters placed at accessible positions in the product.

Electronic components are particularly sensitive to overexposure to radiation during sterilization. Another embodiment of this invention uses sterilization simulations to evaluate and guide the design of protective shielding for electronics or other radiation-sensitive components. Each proposed shielding design can be simulated to determine its effectiveness while maintaining the appropriate level of sterility.

Certain embodiments of this invention will use the simulated dose values to estimate the impact on the product's functionality. This is typically done with the measured dose values, but because simulations are the only way to obtain the full, three-dimensional dose distribution (since measurements are limited to the regions in which dosimeters can be placed), the estimation of the product's functionality in experimentally inaccessible regions is enabled. Because the simulation only outputs relative dose values, the simulated values need to be calibrated against experimental values to obtain absolute dose values.

During the design and engineering of the product, the product is subjected to a regime of tests, e.g. to ensure that its functionality meets its specifications. The simulation of the sterilization process as one of these tests is included, to be implemented following each design change. This subjects the product to a virtual sterilization test which anticipates the design change's influence on the dose distribution 140. In this way, it can be continually ensured that each design change does not have a detrimental effect on the dose distribution. If a detrimental effect is observed, the simulations can guide the product design to achieve the desired functionality without compromising the sterilization process.

Similarly, the simulations of the sterilization process is included into the design of the product's packaging 150. In the same way, the output of the sterilization simulations can guide the choice of packaging materials and configuration by providing rapid feedback on each design choice's impact on the dose distribution.

Due to the nature of the sterilization process (e.g. the packaged product moving through the radiation beam on a conveyor belt), the product can move within its packaging. This results in different units having slightly different positions and orientations within their packaging. Computer simulations are used to study the influence of this on the resulting dose distributions. By systematically varying the position and orientation of the product within its packaging in the simulation and simulating the dose distribution for each case, the reliability and robustness of the sterilization process can be studied.

For cost reduction, it is beneficial to choose a packing configuration (e.g. the placement of multiple packaged units within a container) that allows for the highest throughput. Typically, the ideal packing configuration is found through experimental trial-and-error. This embodiment can guide this process by testing any potential packing configuration in silico, which removes the need to perform time- and cost-consuming sterilization measurements 160.

Often it is unclear to the manufacturer which is the best sterilization method for their product (for example, electron-beam versus gamma ray). Computer simulations are used to guide this choice by comparing the dose distributions produced by different types of radiation. This information encourages an informed decision about the appropriate sterilization method.

Figure 2:
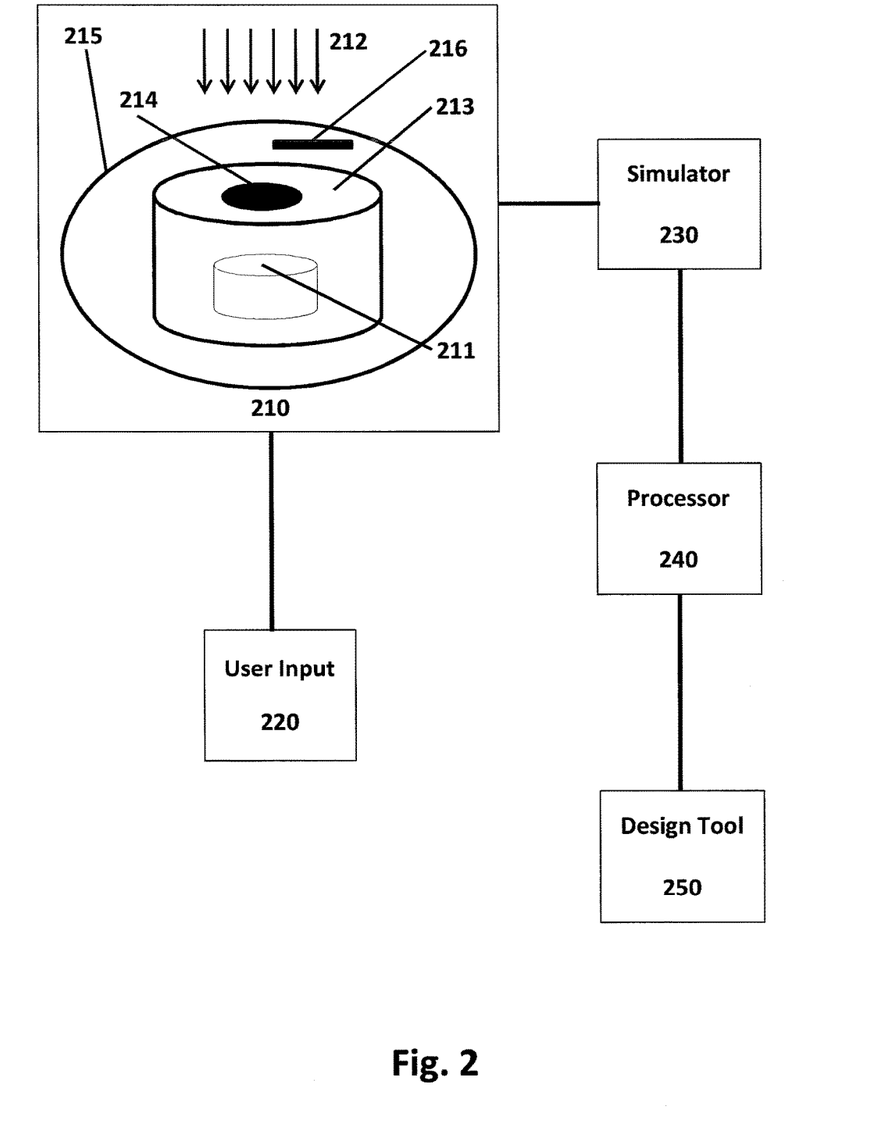
FIG. 2 is a diagram showing an exemplary ionizing radiation control system of one embodiment of the present invention.

FIG. 2 is a diagram showing an exemplary ionizing radiation control system of one embodiment of the present invention. In this embodiment, ionizing radiation control system 200 can comprise display device 210, user input 220, simulator 230, processor 240 and design tool 250. User input 220 can be coupled to display device 210 or can be coupled to simulator 230, processor 240 or design tool 250 or any combination of the foregoing. Simulator 230 can be coupled to processor 240 and processor 240 can be coupled to design tool 250. Display device 210 can be coupled to simulator 230, processor 240 or design tool 250 or any combination of the foregoing.

Display device 210 can display a digital representation of an inanimate object. The inanimate object can be solid, crystalline, metallic, amorphous, polymer, organic, inorganic, liquid-filled, gas-filled or any combination thereof. The inanimate object can be a medical device, a pharmaceutical, a laboratory component or other object. The inanimate object can comprise a void with interior surface 211. The void can be completely enclosed by the material of the inanimate object e.g. injector or it can be partially enclosed by the material e.g. needle or tube.

Simulator 230 can be configured to simulate amount of ionizing radiation 212 at surface 213 of the inanimate object from a radiation source. The ionizing radiation can be x-ray radiation, gamma rays, electron beam, positron or other ionizing particles. Processor 240 can be configured to calculate radiation-matter interaction for the material of the inanimate object. It can also be configured to calculate amount of energy deposited at a plurality of locations at the inanimate object. The plurality of locations can be at the surface 213 of the inanimate object or in the volume beneath surface 213 of the inanimate object. It can also be at the interior surface 211 of the inanimate object or in the void beneath or inside interior surface 211. User input 220 can be configured to receive input from a user and design tool 250 can be configured to modify the digital representation of the inanimate object in response to an input from the user.

Ionizing radiation control system 200 or display device 210 can comprise indicator 214 configured to indicate sufficient sterilization of surface 213 of the inanimate object, sufficient sterilization of interior surface 211 of the inanimate object, sufficient sterilization of a volume of the inanimate object, sufficient crosslinking of surface 213 of the inanimate object, sufficient crosslinking of interior surface 211 of the inanimate object, sufficient crosslinking of a volume of the inanimate object, sufficient neutralization or treatment of hazardous waste on surface 213 of the inanimate object, sufficient neutralization or treatment of hazardous waste on interior surface 211 of the inanimate object, sufficient neutralization or treatment of hazardous waste in a volume of the inanimate object.

The digital representation of the inanimate object can be a three dimensional digital model representing the inanimate object formed from a plurality of solid surfaces. The three dimensional digital model can comprise interior surface 211. Ionizing radiation control system 200 or display device 210 can also comprise a digital representation of packaging 215 around the inanimate object. Ionizing radiation control system 200 or display device 210 can also comprise a digital representation of radiation shielding 216 to completely shield or partially shield the inanimate object.

Figure 3:
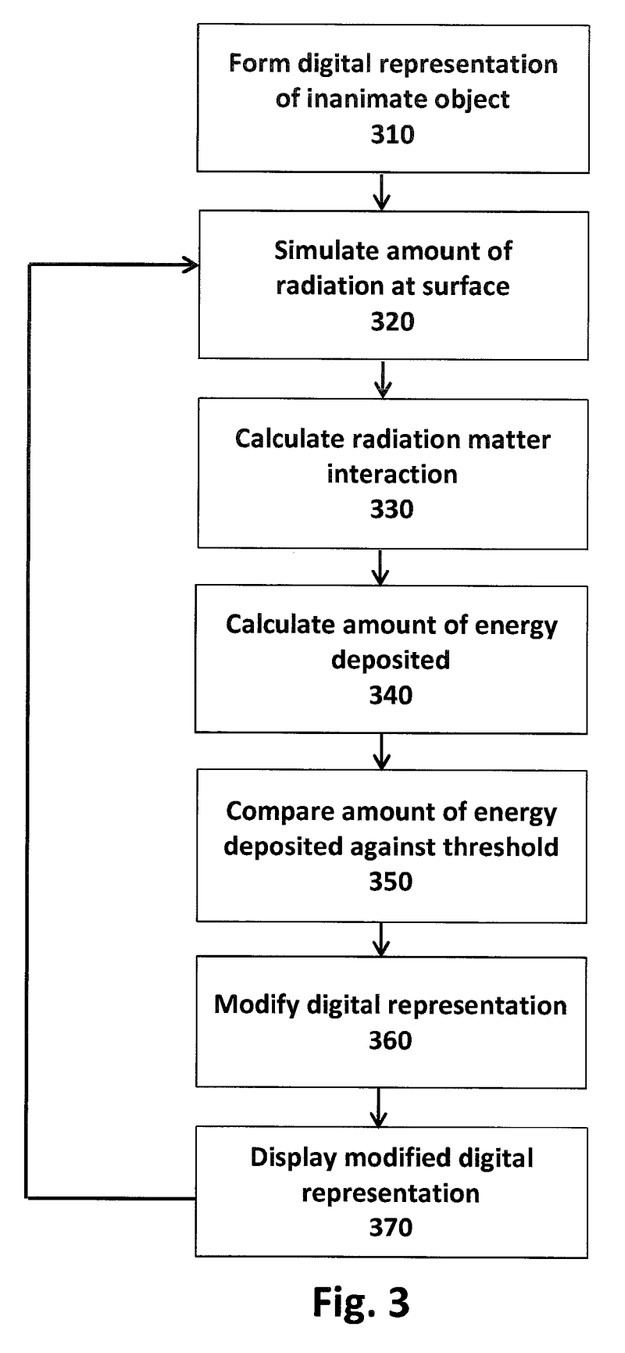
FIG. 3 is a flow diagram illustrating exemplary ionizing radiation control of one embodiment of the present invention.

FIG. 3 is a flow diagram illustrating exemplary ionizing radiation control of one embodiment of the present invention. Ionizing radiation control system 200 or design tool 250 can form digital representation of the inanimate object 310. The digital representation can be two dimensional or can be a three dimensional digital model. A three dimensional digital model can be formed from a plurality of solid surfaces. Boundary representation can be utilized. The inanimate object can be represented by their surfaces, which can be formed as a series of connected facets (typically triangles). Boundary representation solids are also known as tessellated solids. The three dimensional digital model can also be formed from constructive solid geometry. Starting with primitive shapes such as spheres, cubes, cylinders, etc., the inanimate object can be formed by Boolean arithmetic with logical operations such as AND, UNION, etc. The three dimensional digital model can also be voxelized. Voxel-based geometry can be utilized and the inanimate object can be discretized onto a three-dimensional grid.

Voxelized objects can have computational and implementation simplicity. While they can be used in the medical field to represent complex objects such as the human body, they can be ill-suited for medical devices. This is because such devices can often include thin sheets or needles, which can then require minute voxels to achieve the required spatial sampling. This leads to insurmountable memory issues. In order to represent any arbitrary medical device, voxel-based geometry can be difficult to use. Constructive solid geometry objects can have corresponding navigation algorithms that are easy to implement and computationally efficient. However, it can be difficult make a medical device out of spheres and cubes. While it may be possible, constructive solid geometry solids can be limited in their ability to represent realistic objects and such constructions can be incredibly tedious. Furthermore, most modern computer aided design programs do not support constructive solid geometry representations. Boundary representation solids can be an attractive alternative; not only do they constitute the most realistic representation of complex devices and minimize geometry-related errors, they are already used by many popular computer aided design programs. However, they do not lend themselves well to storing volumetric quantities such as dose. Ionizing radiation control system 200 can overlay a three-dimensional voxelized volume to store the dose delivered to each voxel during the simulation. However, this may limit the ability to accurately store dose in objects containing thin sheets or needles. As an alternative, the simulations can accumulate dose in specified parts of the object. The computer aided design model can explicitly include dosimeters and this approach can simulate the dose received by each dosimeter.

Ionizing radiation control system 200 or simulator 230 can simulate amount of radiation at surface 213 of the inanimate object 320. Random sampling and probability distribution can be used to simulate amount of radiation at the surface 213 of the inanimate object. The initial properties of the radiation source can be defined or provided as input. In particular, the initial position, direction, energy, and particle or photon type, collectively known as the particle's or photon's "phase-space information" can be defined or provided. These properties can be specified for each particle or photon in the simulation. The initial properties can be provided in several ways. The initial properties of each particle or photon can be randomly selected from the chosen distribution according to the rules of probability. The user can choose from a set of predefined distributions for each of the phase-space parameters. A data file can be provided that contains measured or simulated phase-space data. The user can provide a mathematical expression that describes the distribution of each of the phase-space parameters.

The radiation source can emit particles such as electrons or positrons or photons. Ionizing radiation control system 200 or simulator 230 can simulate ionizing radiation of electron beams, x-ray beams, gamma beams or other ionizing radiation and can simulate beam energies from 1 keV to 20 keV or any energy or range of energies between such values. The initial spatial distribution of the positions of the particles or photons in the source can be defined in the same absolute coordinate space that the digital representation or computer aided design model is defined, or can be defined relative to a component or sub-assembly in the digital representation or computer aided design model.

Ionizing radiation control system 200 or simulator 230 can calculate radiation-matter interaction for the material of the inanimate object 330. Ionizing radiation control system 200 or simulator 230 can begin by simulating a radiation particle or photon entering the inanimate object or air or gas near the surface of the inanimate object with a specified starting position, energy and direction and calculate a probability distribution for the position, energy and direction. For electron beam source, the type of incident radiation particle is electrons and for gamma or x-ray source, the type of incident radiation is photons. Ionizing radiation control system 200 or simulator 230 can randomly select the distance to the next interaction and transport the particle or photon to the interaction site accounting for geometry of the inanimate object and calculate a probability distribution for the distance. Ionizing radiation control system 200 or simulator 230 can then randomly select the interaction type and simulate the selected interaction and calculate a probability distribution for the interaction. The selected interaction can be elastic or inelastic depending whether the incident particle or photon loses energy. Most interactions are inelastic and it is these interactions that contribute to energy deposited. Some interactions can produce secondary particles or photons. Compton scattering of a photon can produce a secondary electron and the bremsstrahlung effect can produce a secondary photon.

Ionizing radiation control system 200 or simulator 230 can simulate or implement the following interactions for photons: photoelectric absorption, Rayleigh (elastic) scattering, Compton (inelastic) scattering and pair production. For electrons and positrons, the following interactions can be simulated or implemented: elastic scattering, inelastic scattering, Bremsstrahlung emission and positron annihilation. One simpler embodiment of the simulation or simulator would only include electrons and photons. A limited subset of these interactions can be used. A minimum subset of interactions would be: electron elastic scattering, electron inelastic scattering, photoelectric absorption, Compton scattering and Rayleigh scattering. Bremsstrahlung emission can be added as an option. Variance reduction techniques such as interaction forcing, event biasing, importance sampling, and Russian roulette can also be utilized.

Using simulations involving random sampling and probability distribution can be time-consuming. Because quantities such as dose are calculated probabilistically, thousands and thousands of particles or photon can be required to reduce the statistical uncertainty in the simulations. However, each particle or photon can be considered separately. Because of this, the simulations fall under the category of embarrassingly parallel, making them a perfect candidate for utlizing a parallel computing framework, such as using GPUs, e.g. NVIDIA GPUs and CUDA platform.

The collection of faces that make up the entire computer aided design model can be stored in a bounding volume hierarchy to facilitate the efficient propagation of particles on the GPU. This can dramatically reduce the number of facets of the boundary representation solid that need to be checked for intersection during the propagation of particles or photons. The implementation can be implemented to better utilize the new features and abilities of modern GPUs: one such optimization can be the use of the CUDA platform enabled vectorized data structures which allow for faster loads of three dimensional property position data, and the use of corresponding intrinsic floating point math functions on this data. These new optimized intrinsic math functions employ single instruction multiple data capabilities which can perform as many as 8 simultaneous math operations on these vectorized data structures, optimizing the enormous amount of computation required in a particle or photon simulation. The three dimensional representation of the tessellated solids can be stored as "read only" memory as it may not need to be changed during the simulations. This means the storage can utilize the dedicated texture and constant memory caches of GPUs. Because this memory is limited, the representation can be compressed down to a minimal memory footprint without affecting the accuracy of the simulation results.

While the three dimensional representation of the inanimate object can have the largest memory footprint, other input parameters values related to the specific simulation also may be necessarily accessed by the simulated particles or photons. As each group or thread block of particles or photons are being simulated, the physics related input parameters can be stored in the fastest tiers of memory which includes local registers and shared memory. Due to the "embarrassingly parallel" nature of particle or photon simulations with random sampling and probability distributions, there can be an inverse linear relationship between the number of GPUs used for the simulation and the total running time of the simulation. Generally, the total number of particles or photons simulated can be divided by the number of GPU participating in the simulation with each subset allocated to a distinct GPU computing resource. Each GPU computing node can have its own copy of the input boundary representation geometry data as well as having its own three dimensional output buffer to record the dose deposited during the simulation. Once all groups of simulations are completed by the participating GPU compute nodes, this data can be merged together by a pre-designated "mother" node and made available to the user in a final form.

This "mother node" can comprise enough CPU random access memory to aggregate the results from the participating nodes in an efficient manner. The application can have the ability to query the available hardware resources and use the results to determine the best memory management approach for that system. When multiple GPUs are used for a simulation, the required boundary representation solid data can be stored on each participating device and the code can be written to handle such multi-GPU simulations. For cases where this data is too large to store on a given device, the data can be partitioned into sections which will fit into the systems GPUs memory. For simulations which involve use of more than one workstation, an application program interface (API) for communicating data between the distributed processes such as the Message Passing Interface (MPI) can be used.

The simulations can be run on GPU resources in the cloud. If the user of the simulation tool wishes to utilize GPU resources in the cloud for the simulation, there are versions of MPI libraries such Open MPI which can distribute the workload across cloud environments for high performance computing. Amazon HPC web services offers GPU computing nodes and supports Open MPI, and the software tool can function in this specific cloud environment.

Alternatively, ray tracing method can be utilized for calculating the dose distribution by neglecting all scattering interactions and only accounting for absorption effects. Each radiation particle is restricted to travel in a straight line e.g. "ray." As it propagates through the material of the inanimate object, the deposited energy is calculated based on the tabulated attenuation coefficient of the material and how far the particle or photon propagates through the material. Rays can be sent randomly from the source position or raster-scanned over the inanimate object.

Alternatively, deterministic methods for calculating dose or energy deposited can be utilized to calculate the mean distribution of all particles or photons directly by solving a transport equation. A transport equation that accounts for all the necessary physics is then solved on this grid to calculate the spatial dose distribution. The transport equation can be the Boltzmann transport equation. In general, transport equations describe the macroscopic behavior of radiation particles as they travel through and interact with matter. Due to the complexity of the geometry of the inanimate object, the transport equation cannot be solved analytically, and must be solved numerically. To do so, the particle phase-space is discretized onto a grid. The accuracy of deterministic methods is limited by how fine the grid used for the discretization is. Deterministic methods do not suffer from any statistical uncertainty.

Ionizing radiation control system 200 or processor 240 can calculate amount of energy deposited at a plurality of locations at the inanimate object 340. The plurality of locations can be at a surface 213 of the inanimate object, just above the surface 213, just beneath the surface 213 or in the volume of the inanimate object. The plurality of locations can be within 2.5 cm above the surface 213, within 5 cm above the surface 213, within 7.5 cm above the surface 213 or within 10 cm above the surface 213. Using distance too far from surface 213 may result in insufficient energies at surface 213. With inelastic scattering, when the incident particle or photon bounces off or is absorbed in the gas or air near the surface 213 of the inanimate object or in the material of the inanimate object, energy can be transferred at the location of impact. This energy can be quantified as absorbed dose and can be defined as average amount of deposited energy per unit mass.

Ionizing radiation control system 200 or processor 240 can output the simulation as dose distribution. The distribution of dose can be stored as the total dose received by each component in the inanimate object. The simulation can initialize the dose received by each component to be zero, and then each time a dose-depositing event occurs in the simulation, the dose value corresponding to component in which the event occurred can be increased by the appropriate amount. Certain components representing dosimeters can be included directly in the digital representation or computer aided design model and then the total dose received by each of these dosimeters can be reported. The placement of these dosimeters relative to the device in the digital representation or computer aided design model can mimic the physical placement of dosimeters on a real device during a dose mapping experiment. A supplementary file can be provided that identifies which components in the digital representation or computer aided design model should be treated as dosimeters. Ionizing radiation control system 200 or processor 240 can divide a configurable volume into a mesh and then accumulate the total dose received by each element in the volume mesh. Examples of volume meshes could be a regular grid, voxels or a tetrahedral mesh. The meshing need not be regular and could be adaptive to have finer resolution in areas in which the digital representation or computer aided design model has finer detail. Each mesh element can contain one material to avoid partial volume artifacts. Statistical information about the deposited dose in each component or volume mesh element, such as the standard deviation, mean, and the number of contributing events, can be provided.

Ionizing radiation control system 200 can used to assist in selection of the appropriate type of ionizing radiation, e.g. e-beam vs gamma. For radiation sterilization, medical device and pharmaceutical companies can be faced with the choice of gamma, electron-beam, or x-ray sources. Each of these techniques has its own benefits that might make it the ideal choice for a particular product. Ionizing radiation control system 200 can guide the user toward the most efficient, cost-effective, and reliable sterilization method for a given product. One way to compare gamma, electron-beam, and x-ray sterilization would be to experimentally measure the dose received by a product when exposed to each source. This would involve taking the product to several different facilities and would be an expensive endeavor, and so is not feasible in practice. However, by change the configurable parameters of ionizing radiation control system 200, e.g. the particle or photon type and the system geometry, ionizing radiation control system 200 can directly compare different ionizing radiation sources e.g. gamma, electron-beam, and x-ray sources. This comparison can involve simulating the dose distribution received by the inanimate object for each of the source configurations chosen by the user. The dose quantity or alternatively fluence can be varied by the user or ionizing radiation control system 200. The comparison can output the dose statistics e.g. average dose, maximum/minimum dose, etc.) for each type of ionizing radiation. Ionizing radiation control system 200 can also output the difference in the dose distribution. This could be, for instance, the percent difference in the three dimensional dose distribution, the absolute difference, a list of each component and the difference in the dose received by each type of ionizing radiation, etc.

Ionizing radiation control system 200 or processor 240 can be used to estimate the impact of ionizing radiation on functionality of the inanimate object. Many materials have their physical properties changed when exposed to ionizing radiation. While this is usually an undesired side effect of exposure to ionizing radiation, it can be useful when processing materials. For example, when the polymer chains in plastics are exposed to radiation, "cross-linking" occurs and the plastic hardens, known as curing. The properties affected can be physical, mechanical, chemical, etc. Many plastics can change color when exposed to ionizing radiation. Changes in the constituent materials can influence the functionality of a device. Ionizing radiation control system 200 or processor 240 can calculate the dose distribution in the inanimate object. The calculated dose values in each component can be compared against tabulated data that lists how the properties of the material of the component can change according to the dose received. These tables can be taken from standard data bases, could be measured, or could be simulated. Ionizing radiation control system 200 or processor 240 can then output the new properties of each component of the inanimate object after exposure to radiation, and also the change in properties, e.g. original density=9.0 g/cm$^3$, irradiated density=10.0 g/cm$^3$, change in density=+ 1.0 g/cm$^3$. The user can select which properties they are interested in investigating, and in which components. Experimentally, the dose can only be measured on surfaces since dosimeters can only be put on top of existing components. However, under one embodiment of the present invention, ionizing radiation control system 200 or processor 240 can simulate the dose within a component, and can estimate how the bulk properties of each component change, not just the surface properties.

Ionizing radiation control system 200 or design tool 250 can modify the digital representation of the inanimate object 360. The modification can be done in response to an input from the user. Ionizing radiation control system 200 or display device 210 can display the modified digital representation of the inanimate object 370. Ionizing radiation control system 200 or simulator 230 can simulate amount of radiation at the surface 213 of the inanimate object 320 and can calculate radiation-matter interaction for the material of the inanimate object 320. Ionizing radiation control system 200 or processor 240 can calculate amount of energy deposited at a plurality of locations at the inanimate object 340 and can compare amount of energy deposited at each of the plurality of locations at the inanimate object against a dose threshold 350. Different design configurations and material selection can be simulated or selected by the user and its effect on sterilization, crosslinking or waste treatment process can be determined or simulated.

Ionizing radiation control system 200 or design tool 250 can utilize files with computer aided design formats such as ISO 10303 or Standard for the Exchange of Product model data (STEP) or STereoLithography (STL) format. The computer aided design files can be an assembly of individual components, an assembly consisting of sub-assemblies, or a collection of individual components. A component can be defined to be a piece of computer aided design model that is composed of a single material. The input can be a single computer aided design file or a number of computer aided design files. If multiple computer aided design files are utilized, they must be defined in the same absolute coordinate space, or a supplementary file must be utilized that lists the geometric transformations (rotations and translations) that are required to bring the various computer aided design files into the same coordinate space.

Ionizing radiation control system 200 or design tool 250 can initially parse the input computer aided design files based on the standardized definition of the file format. The parsing can recursively separate each sub-assembly until it is divided into individual components. The hierarchy of assemblies and sub-assemblies can be stored as auxiliary information. Each component in the computer aided design model can be assigned a single material. If the computer aided design file format contains the material information for some or all of the components, ionizing radiation control system 200 or design tool 250 can take the material information from the computer aided design file during initial processing. If the computer aided design file does not support material information, or if the computer aided design file format supports material information but it has not been provided for some or all of the components, a supplementary file can be used that contains a list of all components in the computer aided design file and assigns them a material.

The material assigned in the computer aided design file or in the supplementary file can be the name of a material or material definition information. If it is the name of a material, an additional material definition file can be provided for each unique material in the computer aided design model. The material definition can contain the density of the material, and its elemental composition. The elemental composition can contain a list of all the elements that are present in the material as well as the proportionate amount of each element in the material. The material can be defined either as a mixture, in the chemistry sense, in which case the fraction by mass of each element can be provided, or as a compound, in the chemistry sense, in which case the number of atoms of each element can be provided. The material definition may also contain additional information such as crystallographic properties, optical properties, electro-magnetic properties, or other properties. Once the entire computer aided design model has been broken down into a hierarchy of individual components, each component can be tessellated into its boundary representation. It can be converted into tessellated boundary surface. The tessellation can be triangular or a polygon mesh. The user can have control over the resolution or number of faces in the tessellation and the tessellation can be adaptive or uniform.

Ionizing radiation control system 200 or processor 240 can compare amount of energy deposited at each of the plurality of locations at the inanimate object against a dose threshold 350. Ionizing radiation control system 200 or processor 240 can also compare against multiple dose thresholds. Dose can be quantified as average amount of deposited energy per unit mass. The dose threshold can be the amount required to achieve sterilization or the amount required to achieve adequate crosslinking of the material of the inanimate object or the amount required to achieve neutralization or treatment of hazardous waste. Ionizing radiation control system 200 or processor 240 can take into account two limits. The first can be a minimum dose that is sufficient to sterilize or kill all contaminants on or in the inanimate object, to achieve adequate crosslinking of the inanimate object or to achieve adequate neutralization or treatment of hazardous waste on or in the inanimate object. The second can be the maximum dose that can be received prior to adversely affecting functionality of the inanimate object since the properties of some materials change when exposed to ionizing radiation. Ionizing radiation control system 200 can ensure that dose deposited on all parts of the inanimate object is within the minimum and maximum dose amounts. Ionizing radiation control system 200 or display device 210 can output the full-three dimensional dose distribution delivered during radiation. It can calculate the maximum and minimum dose values from this distribution and use this information to produce a likelihood that the radiation was safely within regulated limits. This likelihood can account for sources of uncertainty such as the statistical nature of simulations and can provide a prediction of whether or not the inanimate object will pass verification testing. For sterilization, minimum dose can be 15 kGy to 40 kGy. For ionizing radiation treatment of food, maximum dose can be 10 kGy. For crosslinking, minimum dose can be 175 kGy to 275 kGy.

The statistical information of the deposited dose for the entire digital representation or computer aided design model can be calculated. This can include calculating the average dose received by all components in the inanimate object, the total dose received by the inanimate object, and the minimum and maximum dose received by the inanimate object. The calculations can account for the statistics in the calculations of the dose of each constituent component/mesh element. Ionizing radiation control system 200 or processor 240 can take bounds for the dose received by the inanimate object during ionizing radiation as specified by regulations bounds as an input, in which case the minimum and maximum dose calculated by the simulation can be compared against the regulated bounds. The outcome of this comparison can be an estimation of whether or not the simulation dose is within the input bounds. Modern statistical evaluation such as hypothesis testing and interval estimation can be used to estimate the statistical significance of the outcome.

Figure 4:
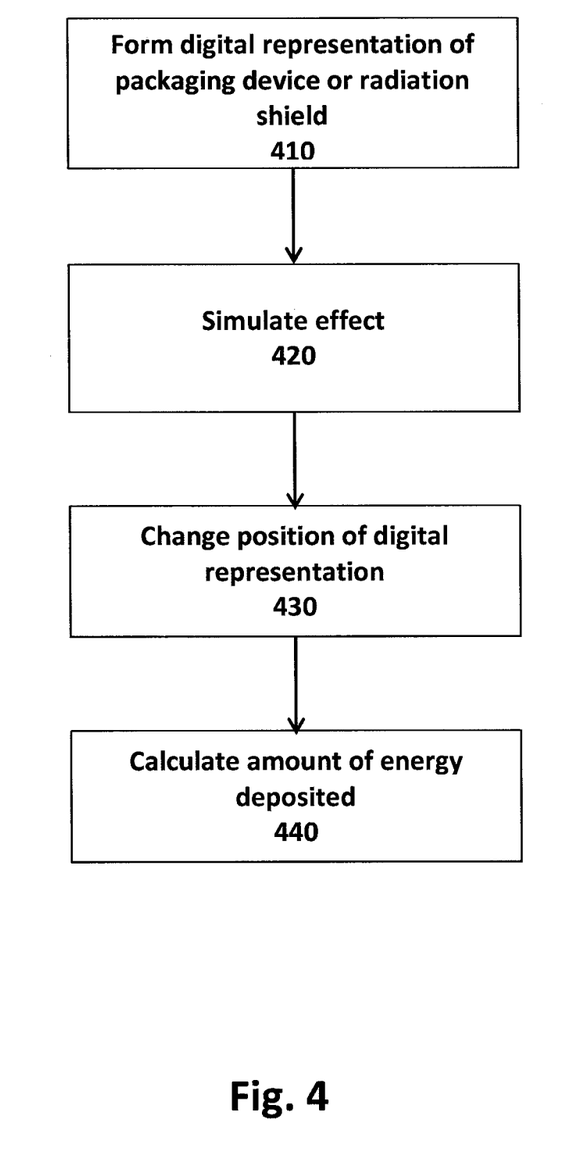
FIG. 4 is a flow diagram illustrating exemplary ionizing radiation control for packaging or radiation shield of one embodiment of the present invention.

FIG. 4 is a flow diagram illustrating exemplary ionizing radiation control for packaging or radiation shield of one embodiment of the present invention. Ionizing radiation control system 200 or design tool 250 can form a digital representation of a packaging device around the inanimate object 410. The package device can be a different material from the inanimate object. Ionizing radiation control system 200 or simulator 230 can simulate effect of the packaging device on the amount of energy deposited at each of the plurality of locations at the inanimate object 420. Instead of or in addition to packaging device, ionizing radiation control system 200 or design tool 250 can form a digital representation of a radiation shield and ionizing radiation control system 200 or simulator 230 can simulate effect of the packaging device on the amount of energy deposited at each of the plurality of locations. The radiation shield can be a different material from the inanimate object and the packaging device. In this manner, the effect of the packaging or radiation shield or both on sterilization, crosslinking or waste treatment process can be determined or simulated.

Ionizing radiation control system 200 or design tool 250 can modify the digital representation of the packaging device or radiation shield. The modification can be done in response to an input from the user. Ionizing radiation control system 200 or display device 210 can display the modified digital representation of the packaging device or radiation shield. Ionizing radiation control system 200 or simulator 230 can simulate amount of radiation at the surface of the inanimate object 320 and can calculate radiation-matter interaction for the material of the inanimate object 320. Ionizing radiation control system 200 or processor 240 can calculate amount of energy deposited at a plurality of locations at the inanimate object 340 and can compare amount of energy deposited at each of the plurality of locations at the inanimate object against a dose threshold 350. Different packaging devices, packaging configurations and packaging materials can be simulated or selected by the user and its effect on sterilization, crosslinking or waste treatment process can be determined or simulated. Likewise, different radiation shields, radiation shield configurations and radiation shield materials can be simulated or selected by the user and its effect on sterilization, crosslinking or waste treatment process can be determined or simulated.

Ionizing radiation control system 200 or design tool 250 can be used to optimize the packing configuration for throughput. For cost reduction, it can be beneficial to choose a packing configuration that allows for the highest throughput. Typically, the ideal arrangement is found through experimental trial-and-error. In addition to being expensive and time-consuming, such an approach might miss the packing configuration that strikes the balance between throughput and efficacy of ionizing radiation for sterility, crosslinking or hazardous waste treatment. The process of choosing the ideal packing configuration can be guided by simulating the three dimensional dose distribution of any potential packing configuration in silico. Each proposed packing configuration can be tested to make sure it passes the specified dose limits, and can be quantified by how densely it packs the products. The density can be quantified by the volume of the smallest bounding box that surrounds the minimum repeating unit of the packing. In this manner, time- and cost-consuming measurements of sterilization, crosslinking or treatment of hazardous waste can be minimized.

Ionizing radiation control system 200 or design tool 250 can be used to guide the design of radiation shielding. As medical devices become more sophisticated, satisfying the sterilization regulations becomes more challenging. For instance, with the rise of wearable technology and combination devices, many medical products have built-in electronics or drugs whose functionality would be compromised if exposed to any radiation during sterilization. As such, many contract sterilization companies are beginning to offer a service to design special shielding to protect part of a medical device during sterilization. While this approach has been demonstrated with moderate success, it is expensive and time-consuming due to the manual, trial and error testing of each shielding design. Furthermore, because the shielding is designed solely based on the experience of the sterilization company, it may not be the optimal design for a given device. However, ionizing radiation control system 200 or design tool 250 can simulate the dose distribution received by the device or inanimate object and the user can guide and optimize the design of radiation shielding. Similarly, depending on the design and composition of the inanimate object, certain parts or regions of the inanimate object can require higher levels of dose than others. By simulating the three dimensional dose distribution received during ionizing radiation, the user could design external filters or blocks of metal to spatially shape the dose distribution.

Ionizing radiation control system 200 or processor 240 can change position of the digital representation 430. Ionizing radiation control system 200 or processor 240 can calculate amount of energy deposited at each of the plurality of locations 440. Changed position of the digital representation can be beneficial to simulate or account for movement or rotation of the inanimate object in packaging device 215 during transport prior to exposure to ionizing radiation. Ionizing radiation control system 200 or processor 240 can be used to estimate the sensitivity of sterilization, crosslinking or hazardous waste treatment to the movement of the inanimate object in packaging. Conveyor belts are often used to move the product across the ionizing radiation beam. The individual inanimate object can move in packaging due to the vibrations of the conveyor belt. Multiple inanimate objects can also move relative to each other in their packaging. One embodiment of the present invention allows the user to input a range of motions for the inanimate object e.g. ±5 degree rotation around the x-axis, ±5 mm translation along z axis, etc. The user can also input how finely these ranges should be sampled. Ionizing radiation control system 200 or processor 240 can then perform a series of simulations by systematically varying the position/orientation of the inanimate object within the specified ranges and calculate the dose distribution for each position. Ionizing radiation control system 200 or processor 240 can determine and output the dependence of the statistics of the dose distribution on the positioning of the inanimate object.

Figure 5:
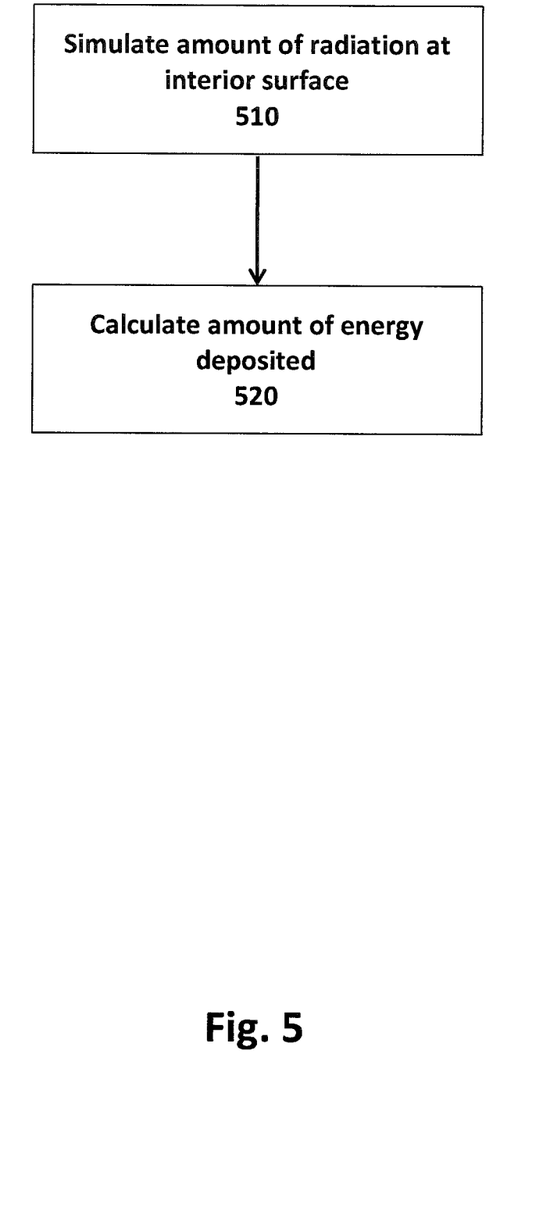
FIG. 5 is a flow diagram illustrating exemplary ionizing radiation control for interior surface of one embodiment of the present invention.

FIG. 5 is a flow diagram illustrating exemplary ionizing radiation control for interior surface of one embodiment of the present invention. Ionizing radiation control system 200 or simulator 230 can simulate amount of radiation at the interior surface 211 of the inanimate object 510. Ionizing radiation control system 200 or processor 240 can calculate amount of energy deposited at each of the plurality of locations 520 and can compare amount of energy deposited at each of the plurality of locations at interior surface 211 against a dose threshold. Calculating amount of energy deposited at each of the plurality of locations at interior surface 211 against a dose threshold can be beneficial to simulate or determine sterilization or waste treatment of inanimate objects with a void partially enclosed by material e.g. needle or tube.

Figure 6:
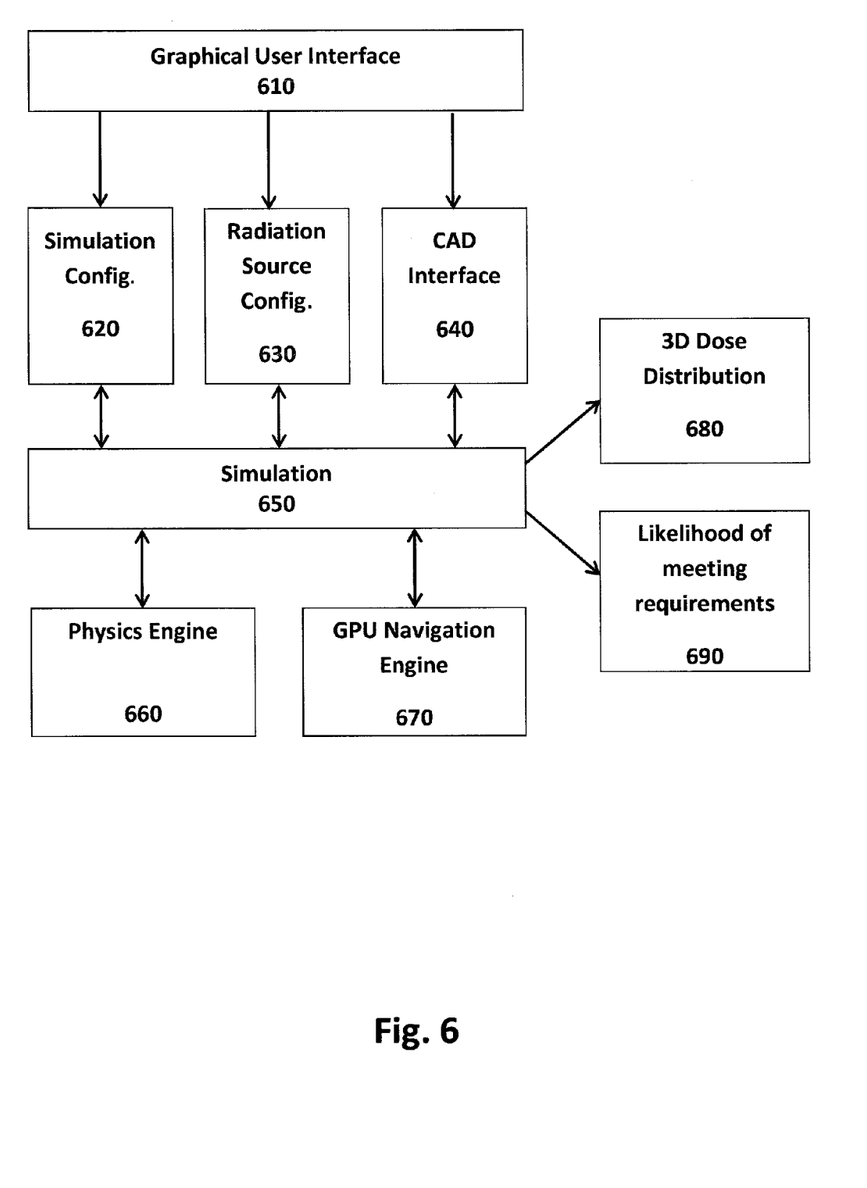
FIG. 6 is a diagram showing an exemplary architecture of ionizing radiation control system of one embodiment of the present invention.

FIG. 6 is a diagram showing an exemplary architecture of ionizing radiation control system of one embodiment of the present invention. Graphical user interface 610 is coupled to simulation configuration 620, radiation source configuration 630 and computer aided design interface 640. Simulation configuration 620, radiation source configuration 630 and computer aided design interface 640 are coupled to simulation 650. Simulation 650 is coupled to physics engine 660 and GPU navigation engine 670. Simulation 650 is also coupled to three dimensional dose distribution 680 and likelihood of meeting requirements 690.

Graphical user interface 610 allows the user to specify the configuration parameters of the simulation 620 (e.g. the type of radiation, the beam energy, the geometry of the setup, etc.), radiation source configuration 630 and to view the results of the simulation. In particular, the system can be pre-configured to the system geometry of a particular system.

Computer aided design interface 640 allows the user to upload a digital representation of the inanimate object in a computer aided design format. There are many benefits to supporting computer aided design format formats. They allow for the most realistic representation of the inanimate object to be exposed to ionizing radiation. Computer aided design formats are the industry standard in mechanical engineering, and so computer aided design interface 640 improves the user's experience by making use of a file format already familiar to them. Support for computer aided design formats allows for simulations to be performed without having a fully engineered or manufactured product.

Achieving sufficient statistical certainty in the simulated dose requires the simulation of many radiation particles or photons. This limits the speed of simulations because modern CPUs are restricted to performing such simulations in a sequential fashion. Ionizing radiation control system 200 can perform the simulations on a GPU through GPU navigation engine 670, making use of the massively parallel architecture of GPUs, allowing for thousands of particles to be simulated simultaneously.

At each step of a radiation particle's or photon's propagation through the inanimate object, the radiation-matter interactions can be calculated by physics engine 660. Accounting for the appropriate physics is essential for accurate dose simulations. An internal GPU-based library can be utilized for simulating particles or photons. Simulation 650 tracks every particle or photon and can output various statistical quantities, such as the fluence of all particles or photons which exit the inanimate object due to scattering. This library can include features required for simulations, such as navigation through computer aided design-formatted objects and the appropriate physics for e-beam and gamma radiation. It can serve as the backbone of GPU navigation engine 670. Additionally, computer aided design interface 640 can extract the geometric information from computer aided design files and represents it in a form amenable to simulations and or simulation 650. This functionality can be integrated into a custom-written Geant4 application that can simulate the dose distribution 680 delivered during radiation. Simulation 650 can output the full-three dimensional dose distribution delivered during radiation 680. It can calculate the maximum and minimum dose values from this distribution and use this information to produce a likelihood that the radiation was safely within regulated limits 690. This likelihood can account for sources of uncertainty such as the statistical nature of simulations and can provide a prediction of whether or not the inanimate object will pass verification testing.

The results and simulations from ionizing radiation control system 200 can be validated through experimental benchmarking. Custom-designed phantoms can be utilized. The phantoms can be designed to estimate the source properties such as energy distribution, spatial distribution, direction distribution or fan beam angle, etc. Experimental benchmarking can be performed on each real-life ionizing radiation system that will be used. The same phantom could be used for each system, or a unique phantom could be designed for each system.

Ionizing radiation control system 200 can used to guide the design of ionizing radiation equipment and facilities for sterilization, crosslinking or hazardous waste treatment. Designing a new ionizing radiation facility can be an expensive endeavor. Simulations can be used to estimate the radiation source parameters, but the dose distribution the source produces is only measured experimentally. Ionizing radiation control system 200 allow for new ionizing radiation systems sterilization, crosslinking or hazardous waste treatment to be tested in silico i.e. without having to invest money to build and experimentally test the systems. Ionizing radiation control system 200 simulate the dose distribution in the irradiation area, and seeing how the dose distribution changes when the system parameters or geometry are changed, the information can be used to evaluate different ionizing radiation systems for sterilization, crosslinking or hazardous waste treatment.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method for x-ray ionizing radiation control comprising:
    forming a digital representation of an inanimate object;
    simulating amount of said x-ray radiation at a surface of said inanimate object;
    calculating radiation-matter interaction for a material of said inanimate object;
    calculating amount of energy deposited at a plurality of locations at said inanimate object;
    modifying said digital representation of said inanimate object in response to an input from a user; and
    displaying said modified digital representation of said inanimate object.

2. The method of claim 1 wherein said plurality of locations at said inanimate object is located at said surface of said inanimate object.

3. The method of claim 1 further comprising:
    comparing amount of energy deposited at each of said plurality of locations at said inanimate object against a dose threshold required to achieve sterilization of said material.

4. The method of claim 3 further comprising:
    forming a second digital representation of a packaging device of a second material around said inanimate object; and
    simulating effect of said packaging device on said amount of energy deposited at each of said plurality of locations.

5. The method of claim 3 further comprising:
    changing position of said modified digital representation of said inanimate object; and
    calculating amount of energy deposited at each of said plurality of locations at said inanimate object in said changed position.

6. The method of claim 1 further comprising:
    comparing amount of energy deposited at each of said plurality of locations at said inanimate object against a dose threshold required to achieve adequate crosslinking of said material.

7. The method of claim 1 further comprising:
    comparing amount of energy deposited at each of said plurality of locations at said inanimate object against a dose threshold required to achieve neutralization of hazardous waste on said material.

8. The method of claim 1 further comprising:
    forming a second digital representation of a radiation shield of a second material; and
    simulating effect of said radiation shield on said amount of energy deposited at each of said plurality of locations.

9. The method of claim 1 further comprising:
    varying dose of said x-ray radiation.

10. The method of claim 1 further comprising:
varying fluence of said x-ray radiation.

11. The method of claim 1 further comprising:
calculating probability distribution of said x-ray radiation on said surface of said inanimate object.

12. The method of claim 1 further comprising:
calculating probability distribution of said radiation matter-interaction resulting from said x-ray radiation on said surface of said inanimate object.

13. The method of claim 1 further comprising:
forming a three dimensional digital representation of said inanimate object.

14. The method of claim 1 further comprising:
forming a three dimensional digital model representing said inanimate object from a plurality of solid surfaces.

15. The method of claim 1 further comprising:
simulating amount of said x-ray radiation at a second plurality of locations on an interior surface of said inanimate object; and
calculating amount of energy deposited at said second plurality of locations on said interior surface of said inanimate object.

16. A system for x-ray ionizing radiation control comprising:
a display device for displaying a digital representation of an inanimate object to a user;
a simulator coupled to said display device configured to simulate amount of said x-ray radiation at a surface of said inanimate object;
a processor coupled to said simulator configured to calculate radiation matter-interaction for a material of said inanimate object and configured to calculate amount of energy deposited at said plurality of locations at said inanimate object;
a user input device coupled to said display for receiving input from said user; and
a design tool configured to modify said digital representation of said inanimate object in response to said input from said user.

17. The system of claim 16 further comprising:
a second digital representation of packaging around said inanimate object.

18. The system of claim 16 further comprising:
a three dimensional digital model representing said inanimate object formed from a plurality of solid surfaces.

19. The system of claim 18 further comprising:
an interior surface in said three dimensional digital model representing said inanimate object.

20. The system of claim 16 further comprising:
an indicator configured to indicate sufficient sterilization of said inanimate object.

* * * * *